United States Patent

Rodelet

Patent Number: 5,962,524
Date of Patent: Oct. 5, 1999

[54] DEPIGMENTING COMPOSITION

[75] Inventor: Jean François Rodelet, Boulogne-Billancourt, France

[73] Assignee: Caster, Paris, France

[21] Appl. No.: 09/215,358

[22] Filed: Dec. 18, 1998

[30] Foreign Application Priority Data

Dec. 24, 1997 [FR] France .................................. 9716475

[51] Int. Cl.⁶ .................................................. A01N 37/02
[52] U.S. Cl. ........................................... 514/547; 514/844
[58] Field of Search ............................... 514/235.5, 316, 514/589, 547, 844; 548/104, 403; 564/56, 47; 544/163

[56] References Cited

U.S. PATENT DOCUMENTS

| | | | |
|---|---|---|---|
| 4,367,239 | 1/1983 | Bregnedal et al. | ...................... 514/589 |
| 4,384,140 | 5/1983 | Bregnedal et al. | ........................ 564/56 |
| 5,023,335 | 6/1991 | Schumacher et al. | ................... 548/104 |
| 5,760,035 | 6/1998 | Rafferty et al. | ...................... 514/235.5 |

*Primary Examiner*—Keith D. MacMillan
*Assistant Examiner*—Vickie Kim
*Attorney, Agent, or Firm*—Jones, O'Keefe, Egan & Peterman, LLP

[57] ABSTRACT

The invention relates to a cosmetic or dermatological composition comprising, in a physiologically acceptable medium, a compound of general formula (I)

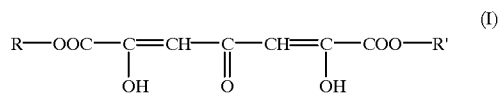

in which the groups R and R' represent, independently of each other, a $C_{1-6}$ alkyl group or a hydrogen atom, or a physiologically acceptable salt of such a compound, this composition being used for depigmenting the skin

16 Claims, No Drawings

DEPIGMENTING COMPOSITION

The present invention relates to a cosmetic or dermatological depigmenting composition containing a novel depigmenting active principle, and to its use for lightening the skin or for treating pigmentation marks.

The control of skin pigmentation phenomena is acquiring ever-increasing importance in cosmetological research, since, for sociocultural or aesthetic reasons, there is an increasing desire for cosmetic products intended to lighten the colour of the skin or to suppress or fade marks caused by pigmentation disorders.

The pigmentation of the skin and the exoskeleton of mammals, and in particular of man, is due to the presence of melanins, which are complex polymer pigments whose colour can range from brown-black (eumelanin) to red (phaeomelanin). The biosynthesis of melanin, melanogenesis, is ensured by specialized cells known as melanocytes which are found in large numbers in the eyes, the hairbulbs and the skin. The various steps of melanogenesis are now relatively well known.

In the various steps of melanogenesis, only the first two reactions are under the control of a metalloenzyme, known as tyrosinase, which oxidizes tyrosine into dihydrophenylalanine (DOPA) and then into dopaquinone. All of the subsequent steps take place spontaneously, without involving an enzyme. Consequently, it is desired to inhibit or stimulate melanogenesis, the regulation is easiest by modifying the activity of tyrosinase.

A certain number of depigmenting active agents which prevent melanin biosynthesis by acting on tyrosinase are known. Some of them, such as kojic acid, suppress the synthesis or maturation of tyrosinase by chelation of the copper ions which are essential for it to function. The others directly inhibit the activity of tyrosinase by behaving as substrate analogues, occupying the active site of the enzyme and competing with tyrosine or DOPA. This is probably the case with hydroquinone, a well-known depigmenting active agent whose use is nowadays strictly controlled on account of its high cytotoxicity, as well as with arbutin (4-hydroxyphenyl -β-D-glucopyranoside), a depigmenting compound extracted from a certain number of plants (see French patent 94/08750).

Japanese patent application No. 63-8317 discloses an agent with skin-lightening power for external use, which contains chelidonic acid as active principle. It has been possible for a long time to prepare this acid, which is present in various plants and can be extracted in particular from chelidoin, by organic synthesis from acetone and ethyl oxalate (E. R. Riegel and M. C. Reinhard, *Journal of American Chemical Society* (1926), 48, pages 1334–1344, and J. Duclaux and J. Barbière, *Bulletin de la Société Chimique de France* (1933), 53, pages 564–569).

The present inventors have observed, unexpectedly, that the main synthetic intermediate compound, diethyl acetone-α,α'-dioxalate, has tyrosinase-inhibiting properties and that it is suitable as an active principle in depigmenting compositions.

The subject of the present invention is consequently a cosmetological or dermatological depigmenting composition containing, as active principle, a compound of acetone-α,α'-dioxalate type and its use for lightening the skin or for treating pigmentation marks.

Another subject of the present invention consists of a process for lightening the skin or a process for the cosmetic or dermatological treatment of pigmentation marks, using the composition defined above.

Other subjects of the invention will become apparent in the light of the description and the examples which follow.

The cosmetic or dermatological compositions of the present invention are characterized in that they comprise, in a physiologically acceptable medium, a compound of general formula (I)

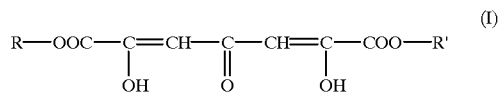

in which the groups R and R' represent, independently of each other, a $C_{1-6}$ alkyl group or a hydrogen atom, or a physiologically acceptable salt of such a compound.

In a preferred embodiment of the present invention, the two radicals R and R', which may be identical or different, represent an alkyl group, which is preferably $C_{1-6}$. Diethyl acetone-α,α'-dioxalate, i.e. a compound of formula (I) in which the two residues R represent an ethyl group, is particularly preferred.

The compositions in accordance with the present invention are preferably in the form of a milk, a cream or a gel.

They preferably contain the active principle in vectorized form, i.e. included in vectors such as liposomes.

The active principle of formula (I) is present in the compositions of the present invention at concentrations of between 0.1 and 5% by weight, preferably between 0.25 and 3% by weight.

The physiologically acceptable medium for the compositions consists mainly of water. Additives commonly used in cosmetics or dermopharmacy can be incorporated therein. These additives are, for example, plant or mineral oils (liposomes), emulsifiers, thickeners, preserving agents, dyes, fragrances, antiseptics, pH regulators, etc.

The efficacy of the novel active principle of the present invention was tested in vitro by measuring its power to inhibit the tyrosinase-tyrosine enzymatic reaction and the tyrosinase-DOPA reaction, and by evaluating its depigmenting power on human skin explants.

The in vivo depigmenting effect was determined according to the standard method for measuring the pigmentation of the tails of black mice.

For the in vivo and in vitro tests on live material, the reference substance used was hydroquinone, which is a known depigmenting active agent with a certain level of cytotoxicity. In all cases, the preferred depigmenting active principle of the present invention turned out to be of equivalent or even better efficacy than hydroquinone, for applied concentrations less than those of hydroquinone.

The evaluation of the toxicity of the active principle of the present invention, administered orally to rats, gives 50% lethal dose values ($LD_{50}$) of greater than 2000 mg/kg. Diethyl acetone-α,α'-dioxalate is thus not classed as a risk product.

Another advantage of the preferred active principle of the present invention, besides its satisfactory efficacy and the absence of toxicity, lies in its ease of preparation, since this involves a simple organic synthesis procedure in a single container using inexpensive chemical compounds such as acetone and ethyl oxalate, and giving good yields (70%). In this, it differs advantageously from depigmenting active principles extracted from plant materials, such as arbutin, whose extraction requires sizeable means and provides small amounts of active principle.

The examples which follow are intended to illustrate the invention without, however, being limiting in nature.

PREPARATION EXAMPLE

Preparation of diethyl acetone-α,α'-dioxalate 58 g of acetone, 150 g of diethyl oxalate and 273 g of a solution obtained by dissolving 136 g of sodium ethoxide in 410 g of anhydrous absolute ethanol (solution A) are successively added to a two-liter reactor fitted with a stirring system and a reflux condenser and heated with a water bath. The reaction mixture is heated to 75° C. After a few minutes the solution becomes cloudy. A further 160 g of diethyl oxalate and the rest of solution A, heated, if necessary to 60° C., are then added. Vigorous stirring of the mixture is continued while maintaining the temperature at 75° C. A large amount of a greenish-yellow precipitate forms, which results in almost total setting to a solid. The reaction mixture is left to cool, after which a mixture of 300 ml of concentrated hydrochloric acid (d=1.18) and 800 g of crushed ice is added thereto. This mixture is stirred for at least 2 hours in order to neutralize the sodium ethoxide.

The precipitate is filtered off on a sinter funnel and is washed three times with 1 liter of weakly acidic (pH=6) ice-cold water and then once with 1 liter of ice-cold water at pH 7.

The precipitate is left to dry for one week at room temperature.

180 g of a beige-yellow precipitate (70% yield) are thus obtained.

$^1$H NMR:

chemical shift in ppm relative to TMS (250 MHz in CDCl$_3$): 1.40 (6H, triplet), 4.30–4.45 (4 H, quartet), 6.38 (2 H, singlet);

$^{13}$C NMR

δ in ppm relative to TMS (300 MHz in CDCl$_3$): 14.147; 62.849; 104.100; 161.611; 162.131; 196.496;

FORMULATION EXAMPLES

EXAMPLE 1

| depigmenting cream I | g per 100 g |
| --- | --- |
| diethyl acetone-α,α'-dioxalate | 3.00 |
| demineralized water | 70.00 |
| sesame oil | 17.00 |
| cetearylglucoside | 3.00 |
| cetyl alcohol | 2.00 |
| lanolin | 1.50 |
| hydrogenated coconut oil | 1.50 |
| sorbitol PEG-9 oleate | 1.20 |
| preserving agent | 0.50 |
| xanthan gum | 0.30 |
| fragrance | q.s. |

EXAMPLE 2

| depigmenting milk II | g per 100 g |
| --- | --- |
| liposomes containing a 5% dose of active agent | 20.00 |
| demineralized water | 61.70 |
| liquid petroleum jelly | 15.00 |
| cetyl alcohol | 2.00 |
| preserving agent | 0.50 |
| fragrance | q.s. |

EXAMPLE 3

| depigmenting milk III | g per 100 g |
| --- | --- |
| liposomes containing a 5% dose of active agent | 5.00 |
| demineralized water | 61.30 |
| liquid petroleum jelly | 25.00 |
| sorbitol polyoxyethyleneglycerol isostearate | 2.50 |
| beeswax | 2.50 |
| propylene glycol | 2.00 |
| magnesium sulphate | 0.70 |
| sorbitol PEG-7 oleate | 0.50 |
| preserving agent | 0.50 |
| fragrance | q.s. |

EXAMPLE 3

| depigmenting milk IV | g per 100 g |
| --- | --- |
| liposomes comtaining a 5% dose of active agent | 10.00 |
| demineralized water | 69.50 |
| liquid petroleum jelly | 10.00 |
| S.E. glyceryl stearate | 5.50 |
| lanolin | 2.00 |
| petroleum jelly | 2.00 |
| preserving agent | 0.50 |
| carbomer | 0.25 |
| triethanolamine | 0.25 |
| fragrance | q.s. |

For the preparation of these four emulsified products, a standard process for preparing emulsions is used. The water, on the one hand, and the fatty substances, on the other hand, are heated separately to 80° C. The two parts are then combined with stirring in a stirrer (such as a turbomixer or a planetary mixer) while cooling at the same time. When the temperature reaches 30° C.–40° C., the active agent is added, either in pure form (depigmenting emulsion I) or in vectorized form (depigmenting emulsions II–IV), along with the fragrance. Stirring is continued until the mixture has cooled completely.

The products obtained are pale-yellow to light-beige in colour.

The liposomes containing 5% diethyl acetone-α,α'-dioxalate used for the Formulation Examples 2 to 4 have the following composition:

| ingredients | g per 100 g |
| --- | --- |
| demineralized water | 56.3 |
| butylene glycol | 30.5 |
| soybean lecithin | 5.0 |
| diethyl acetone-α,α'-dioxalate | 5.0 |
| wheat protein BPM | 2.0 |
| phenonip | 0.5 |
| xanthan gum | 0.5 |
| Coletica microbiocide | 0.2 | in vitro inhibitory activity of diethyl acetone-α,α'-dioxalate on tyrosinase

I. Inhibition of the L-DOPA-tyrosinase reaction

The inhibition of tyrosinase with diethyl acetone-α,α'-dioxalate in the oxidation reaction of L-DOPA into dopaquinone is revealed by thin layer chromatography.

10 μl of a 1% solution of diethyl acetone-α,α'-dioxalate in ethanol (at 96%) is deposited onto G60 silica gel plates. The migration solvent is a butanol/water/acetic acid mixture (4/1/1, v/v/v) which is migrated to a height of 10 cm. After drying, an L-DOPA solution (1 M) is sprayed over the entire plate, followed by a tyrosinase solution (238 IU/ml). Exposure to daylight reveals a white band with an $R_f$ in the region of 0.80 on a brown background. This white spot is due to the absence of tyrosinase activity converting the L-DOPA substrate into dopaquinone, the molecule which spontaneously converts into a brown pigment (brown background) in the presence of light. The acetone-α,α'-dioxalate thus effectively inhibits the DOPA-tyrosinase reaction.

II. Inhibition of the tyrosine-tyrosinase reaction

The inhibition of tyrosinase with diethyl acetone-α,α'-dioxalate in the hydroxylation reaction of tyrosine into DOPA is revealed by absorption spectrophotometry in the visible range. This is a spectrophotometric assay (absorbance at 477 nm) of the melanin produced in vitro by tyrosinase from the tyrosine substrate.

In order to show that, in the concentration range studied, the absorbance at 477 nm is directly proportional to the activity of tyrosinase, a calibration curve is established using increasing known amounts of tyrosinase.

For this, the following enzyme and substrate solutions are prepared:

| tyrosinase stock solution: | |
|---|---|
| tyrosinase (at 2400 IU/mg) | 10 mg |
| bis Tris buffer (0.1M, pH 6.5) | 1 ml |
| water-q.s. | 50 ml |
| tyrosine stock solution: | |
| L-tyrosine | 0.04 g |
| water-q.s. | 100 ml |

2.0 ml of bis Tris buffer (0.1 M, pH 6.5) and 5.0 ml of tyrosine stock solution are added to 0 ml, 1.2 ml, 2.0 ml and 2.5 ml of tyrosinase solution and the mixtures are each completed with water to a total volume of 10.0 ml.

These mixtures are incubated for 1 hour and 30 minutes at 37° C. on a water bath and are then rapidly cooled to 4° C. Measurement of the absorbance of the solutions at λ=477 nm relative to a solution free of tyrosinase makes it possible to plot a calibration curve characterized by the curve equation $y=0.813x+1.27 \times 10^{-3}$ and by a correlation coefficient equal to 0.999.

The following solutions are then prepared:
Control solution (100% tyrosinase activity):

| tyrosine stock solution | 5.0 ml |
|---|---|
| tyrosinase stock solution (at 96 IU/ml) | 2.0 ml |
| bis Tris buffer (0.1M, pH 6.5) | 2.0 ml |
| water-q.s. | 10.0 ml |

Solution to be ascertained:

| diethyl acetone-α,α'-dioxalate at 2.58% in alocohol | 2.0 ml |
|---|---|
| tyrosine stock solution | 5.0 ml |
| tyrosinase stock solution (at 96 IU/ml) | 2.0 ml |
| bis Tris buffer (0.1M, pH 6.5) | 2.0 ml |

These two solutions are incubated for 1 hour 30 minutes on a water bath at 37° C. The solutions are rapidly cooled to 4° C. and the absorbance at 477 nm is then read, taking a blank free of tyrosinase as reference. The results of five identical tests carried out under these conditions are given in Table 1 below.

TABLE 1

| Test | Absorbance at 477 nm control solution | Absorbance at 477 nm solution to be assayed |
|---|---|---|
| 1 | 1.23 | ≈0 |
| 2 | 1.16 | ≈0 |
| 3 | 1.16 | ≈0 |
| 4 | 1.23 | ≈0 |
| 5 | 1.16 | ≈0 |
| mean | ≈1.16 | ≈0 |

These results show that the diethyl acetone-α,α'-dioxalate effectively inhibits the in vitro production of melanin by tyrosinase from L-tyrosine.

Depigmenting power of diethyl acetone-α,α'-dioxalate in vitro on skin explants

The inhibitory activity of diethyl acetone-α,α'-dioxalate on tyrisonase in melanocytes was evaluated by a histological study on skin explants.

After thawing and fixing for 30 minutes in 10% (w/v) formaldehyde solution, human skin explants obtained from an abdominoplasty are incubated for 15 hours at 37° C. in the presence of 0.005 M of L-DOPA and of the test products.

The diethyl acetone-α,α'-dioxalate is used at concentrations of 0.5%, 1% and 2% (w/v) in a 10% (v/v) solution of DMSO in water.

Hydroquinone, a known tyrosinase inhibitor, is used as reference product, at a concentration of 1.1% (w/v) in a 10% (v/v) solution of DMSO in water.

Control explants incubated only in the presence of 0.005 M of L-DOPA are prepared in parallel.

For the histological examination, 4 μm thick slices are taken from explants included in paraffin and the slices are stained with cresyl violet.

Optical microscopy photographs in white light allow a visual evaluation of the coloration of the melanocytes reflecting the tyrosinase activity. The results are summarized in Table 2 below.

TABLE 2

| product | tyrosinase activity |
|---|---|
| control (absence of inhibitor) | +++ |
| 1.1% hydroquinone | 0 |
| diethyl acetonedioxalate | |
| at 0.5% | 0 |
| at 1.0% | 0 |
| at 2.0% | 0 |

+++: very intense oxidation reaction of the DOPA
0: no oxidation reaction of the DOPA It is seen that, under the test conditions, the diethyl acetone-α,α'-dioxalate tested at proportions of 0.5%, 1.0% and 2% totally inhibits the tyrosinase activity.

Depigmenting power of diethyl acetone-α,α'-dioxalate in vivo on the tails of black mice The depigmenting efficacy of diethyl acetone-α,α'-dioxalate was tested for two compositions containing the active principle in a form vectorized in liposomes, in comparison with a commercial product reputed to be effective, containing hydroquinone (Correcteur anti-taches Liérac [Liérac blemish corrector]—ref. L 908/1).

Composition 1: gel containing 99.0% of liposomes containing a 0.5% dose of diethyl acetone-α,α'-dioxalate Composition 2: emulsion containing 10.0% of liposomes containing a 0.5% dose of diethyl acetone-α,α'-dioxalate Reference product: composition containing 2% hydroquinone Each composition is applied daily for 28 days to the tail of four black mice. For each mouse, the lightness parameter L* is measured on day D0, D15 and D28 using a chromameter.

The efficacy (as a %) of each product is calculated according to the following formula:

$$E\% = ((E_{DY} - E_{DO})/E_{DO})100$$

Table 3 below shows the values of the parameter L* obtained for each product, as well as the efficacy (E %) after 15 and 28 days of treatment. Each value represents the mean standard deviation calculated for 4 mice.

TABLE 3

|  | reference product (2% hydroquinone) | | | composition 1 (0.05% active principle) | | | composition 2 (0.5% active principle) | | |
| --- | --- | --- | --- | --- | --- | --- | --- | --- | --- |
| day | D0 | D15 | D28 | D0 | D15 | D28 | D0 | D15 | D28 |
| mean L* | 43.2 | 45.5 | 44.6 | 42.8 | 45.8 | 46.8 | 39.8 | 45.3 | 47.1 |
| ± standard deviation | ±1.5 | ±1.9 | ±2.1 | ±0.8 | ±0.4 | ±0.8 | ±1.0 | ±0.6 | ±0.8 |
| E% |  | 5.3 | 3.2 |  | 7.1 | 9.5 |  | 13.8 | 18.3 |

These results show that the two compositions containing the active principle of the present invention give better results than the product of the prior art, and do so for lower application concentrations. It is also found that diethyl acetone-α,α'-dioxalate acts in a dose-dependent manner, since a concentration ten times as great increases the efficacy by a factor of two.

It is clearly understood that the preceding description has been given purely for illustrative purposes and without any limitation being implied, and that variants or modifications may be made thereto in the context of the present invention.

I claim:

1. Cosmetic or dermatological composition, characterized in that it comprises, in a physiologically acceptable medium, a compound of general formula (I)

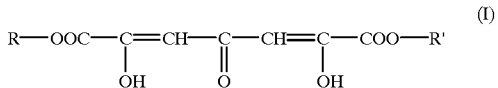

in which the groups R and R' represent, independently of each other, a $C_{1-6}$ alkyl group or a hydrogen atom, or a physiologically acceptable salt of such a compound.

2. Composition according to claim 1, characterized in that the two radicals R and R' represent an alkyl group.

3. Composition according to claim 2, characterized in that the two radicals R and R' represent an ethyl group.

4. Composition according to claim 1 characterized in that it is in the form of a milk, a cream or a gel.

5. Composition according to claim 1, characterized in that it contains the compound of formula (I) in vectorized form in liposome.

6. Composition according to claim 1, characterized in that it contains the compound of formula (I) in a proportion of from 0.1 to 5% by weight.

7. Composition according to claim 1, characterized in that the physiologically acceptable medium comprises water and can optionally comprise other cosmetic or dermatological adjuvants.

8. Process for lightning the skin or for the cosmetic treatment of skin marks, characterized in that a composition according to claim 1 is applied to the skin.

9. Composition according to claim 1, characterized in that it contains the compound of formula (I) in a proportion of from 0.25 to 3% by weight.

10. A method of preparation for a dermatological formulation, comprising: preparing a composition comprising, in a physiologically acceptable medium, a compound of general formula (I)

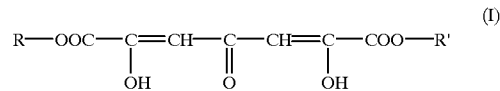

in which the groups R and R' represent, independently of each other, a $C_{1-6}$ alkyl group or a hydrogen atom, or a physiologically acceptable salt of such a compound.

11. The method according to claim 10 wherein R and R' represent an ethyl group.

12. The method according to claim 10 wherein the composition is in the form of a milk, a cream or a gel.

13. The method according to claim 10 wherein the composition contains the compound of formula (I) in vectorized form in liposomes.

14. The method according to claim 10 wherein the composition contains the compound of formula (I) in a proportion of from 0.1 to 5% by weight.

15. The method according to claim 10 wherein the composition contains the compound of formula (I) in a proportion of 0.25 to 3% by weight.

16. The method according to claim 10 wherein the physiologically acceptable medium comprises water and can optionally comprise other cosmetic or dermatological adjuvants.

* * * * *